United States Patent [19]

Marsh

[11] Patent Number: 4,506,540
[45] Date of Patent: Mar. 26, 1985

[54] LIQUID SENSOR AND THE USE THEREOF IN CONTROLLING THE CORROSION OF PIPELINES

[75] Inventor: Glenn A. Marsh, Fullerton, Calif.

[73] Assignee: Union Oil Company of California, Los Angeles, Calif.

[21] Appl. No.: 460,131

[22] Filed: Jan. 24, 1983

[51] Int. Cl.³ ............................................. G01N 27/00
[52] U.S. Cl. ...................................... 73/29; 340/604; 422/53
[58] Field of Search .................. 73/29, 73, 86, 61.2; 324/65 R, 65 CR; 422/10, 53; 436/6; 340/604

[56] References Cited

U.S. PATENT DOCUMENTS

| | | | |
|---|---|---|---|
| 3,166,485 | 1/1965 | Lloyd | 324/65 CR |
| 3,599,862 | 8/1971 | Hogan et al. | 340/604 |
| 3,793,586 | 2/1972 | Heeps | 340/604 |
| 3,914,982 | 10/1975 | Zanetti | 324/65 R |
| 3,996,124 | 12/1976 | Eaton et al. | 324/65 CR |
| 4,356,834 | 11/1982 | Lemay | 73/29 |
| 4,373,392 | 2/1983 | Nagamoto | 324/65 R |

Primary Examiner—Stephen A. Kreitman
Attorney, Agent, or Firm—Robert J. Baran; Gregory F. Wirzbicki; Dean Sandford

[57] ABSTRACT

A liquid water sensor, useful for indicating a corrosive condition in a natural gas pipeline, comprises a plurality of electrically conductive members spaced from each other by an insulating medium and in series with an electrical continuity detector. The conductive members are spaced at a distance sufficient to enable a droplet or film of water to bridge such conductive members to provide a conductive pathway therebetween and thereby provide a signal at the continuity detector. An electrical circuit is also provided which includes a heater for heating the conductive members to evaporate liquid water therefrom and an output circuit for indicating whether liquid water was present or another conductive material having a boiling point greater than water, e.g. ferrous sulfide, continues to provide a conductive pathway between the conductive members after cessation of heating.

19 Claims, 3 Drawing Figures

LIQUID SENSOR AND THE USE THEREOF IN CONTROLLING THE CORROSION OF PIPELINES

BACKGROUND OF THE INVENTION

1. Field of the Invention

This invention relates to a liquid water sensor for the prevention of corrosion in a pipeline used to transport a carbon dioxide-containing gas, i.e., natural gas. This invention further relates to an electrical circuit to determine whether liquid water is present at the liquid water sensor or another conductive material has fouled the sensor.

2. Discussion of the Art

Natural gas is a naturally occurring mixture of condensible hydrocarbons, and hydrocarbon and non-hydrocarbon gases found in the porous geological formations beneath the earth's surface, often in association with petroleum. To obtain a marketable product, the raw natural gas flowing from gas or oil wells must be gathered to control areas, and processed to remove water vapor, inert or poisonous constituents and condensible hydrocarbons. Once processed, the gas is principally methane in admixture with small amounts of ethane, propane, butanes, pentanes, carbon dioxide and nitrogen. The processed gas can be easily transported from producing areas to the market through underground pipelines for use in heating residential and commercial facilities and/or as a feed stream for various chemical processes.

It is critical that some water vapor be removed from the natural gas before transporting by pipeline since, at the operating pressures of commercial pipelines, ice-like gas hydrate crystals form at temperatures well above 0° C. The buildup of these ice-like crystals may restrict or stop the gas flow. Carbon dioxide and nitrogen are inert gases which are removed from raw natural gas to improve the heating value of the remaining gas stream, e.g. it is common practice to limit the inert gases to three percent of the total gas volume. Hydrogen sulfide is also removed from raw natural gas because it is extremely poisonous. It is also well known that, in the presence of water, hydrogen sulfide and carbon dioxide are corrosive.

Unpurified natural gas, as in gas gathering systems, is dehydrated by passing through a solvent for water. For example, water may be removed by absorption in a hygroscopic liquid such as diethylene glycol or triethylene glycol or by adsorption on an activated solid such as silica gel, activated alumina, or a molecular sieve.

Solvents are also used to remove the so-called acid gases, carbon dioxide and hydrogen sulfide. However, in a typical oil or gas field, gas is gathered in a network of pipelines and is dehydrated at some point before the gas is transported to a central processing station for acid gas removal. The dehydration is accomplished in field installations which require monitoring for effectiveness. Failure of the dehydration equipment (or improper operation of it) will allow liquid water to exist in the pipeline downstream from the dehydration equipment. Since the gas not uncommonly contains carbon dioxide and often hydrogen sulfide as well in the gas gathering system, the pipeline transporting the gas could corrode if a liquid water phase is allowed to exist. The corrosion products would include ferrous carbonate and ferrous sulfide.

Thus it is an object of this invention to provide a novel water sensor for the detection of liquid water in a natural gas pipeline used in transporting a carbon dioxide-containing gas.

It is another object of this invention to detect liquid water in the presence of other electrically conductive materials having a boiling point greater than the boiling point of water.

It is another object of this invention to provide an electrical circuit for automatically detecting the presence of an electrically conductive material in a pipeline and determining whether such electrically conductive material is liquid water or an electrically conductive material such as ferrous sulfide.

It is another object of this invention to provide a method of preventing corrosion in a pipeline utilized to transport a carbon dioxide-containing gas by monitoring for the presence of liquid water and adjusting the dew point of said gas to evaporate said liquid water.

Other objects and advantages of the instant invention will become apparent from the following description taken in connection with the accompanying drawings wherein it is set forth by way of illustration and example certain embodiments of this invention.

SUMMARY OF THE INVENTION

The instant invention provides a liquid water sensor for use in a pipeline utilized to transport a carbon dioxide-containing gas which comprises:

(a) a plurality of electrically conductive members spaced from each other by an insulating medium, said conductive members being serially connected and spaced at a distance enabling a droplet or film of water to bridge said conductive members to provide a conductive pathway therebetween and (b) an electrical continuity detector being serially connected to each conductive member.

Preferably said liquid water sensor comprises a plurality of conductive members serially connected in alternating pairs.

The instant invention also provides a liquid water sensor for inserting into a natural gas pipeline and detecting liquid water in the presence of other conductive materials having a boiling point higher than water which comprises:

(a) a hollow cylindrical housing having an open end and being adapted for insertion into the wall of a natural gas pipeline with said open end exposed to the interior of said natural gas pipeline, (b) a plurality of electrically conductive members spaced from each other and serially connected in alternating pairs, each of said conductive members being located within said housing and having an edge adapted to be exposed to the interior of a natural gas pipeline, and each edge being spaced from adjacent edges at a distance suitable for bridging by a droplet or film of water to provide a conductive pathway there between, (c) a heating element in proximity to said conductive members and adapted to heat said conductive members to a temperature sufficient to evaporate water from the exposed edges, (d) an insulating medium spacing each conductive member from adjacent conductive members and rigidly affixing said conductive members and said heating element within said housing, (e) means for electrically connecting said conductive members to a continuity detector, and (f) means for connecting said heating element to a power source.

The instant invention further provides an electrical circuit for detecting liquid water in the presence of other conductive materials having a boiling point higher than water comprising:
(a) a power supply,
(b) an electric heater,
(c) the above liquid water sensor or other detecting means for sensing the electrical conductivity of liquid water and other conductive materials, said detecting means being disposed in an operative relationship with said electric heater for heating said detecting means, and
(d) an electrical circuit, interconnecting said power supply, electric heater and detecting means for controlling the heater in response to the detecting means sensing a conductive material, said electrical circuit being operative to cause the heater to heat the detecting means, for a preselected period of time after the detecting means senses a conductive material to vaporize water therefrom, said electrical circuit including an output circuit for indicating either the presence of water or the presence of another conductive material having a boiling point higher than water.

BRIEF DESCRIPTION OF THE DRAWINGS

This invention will be more readily understood by reference to the drawings wherein like numerals refer to like elements and in which.

DETAILED DESCRIPTION OF THE INVENTION

The liquid water sensor of this invention is of primary usefulness in detecting the presence of liquid water in a pipeline used to transport natural gas, especially a carbon dioxide-containing natural gas. However, the liquid water sensor of this invention and the electrical circuit utilized to distinguish between liquid water and other electrically conductive materials may be used in many other applications to determine the existence of liquid water in the presence of other electrically conductive materials having a boiling point higher than water.

Figure 2:
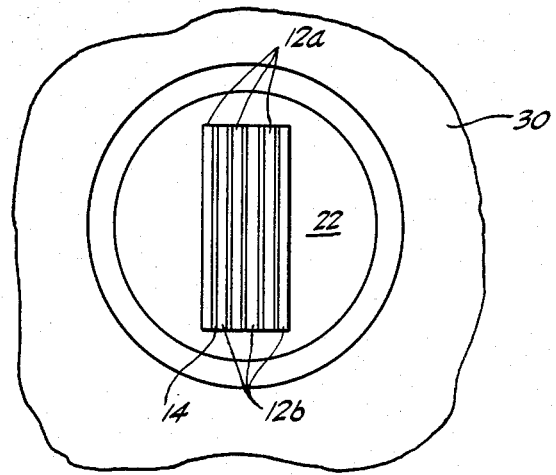
FIG. 2 is a top view of said liquid water sensor of FIG. 1.
Figure 1:
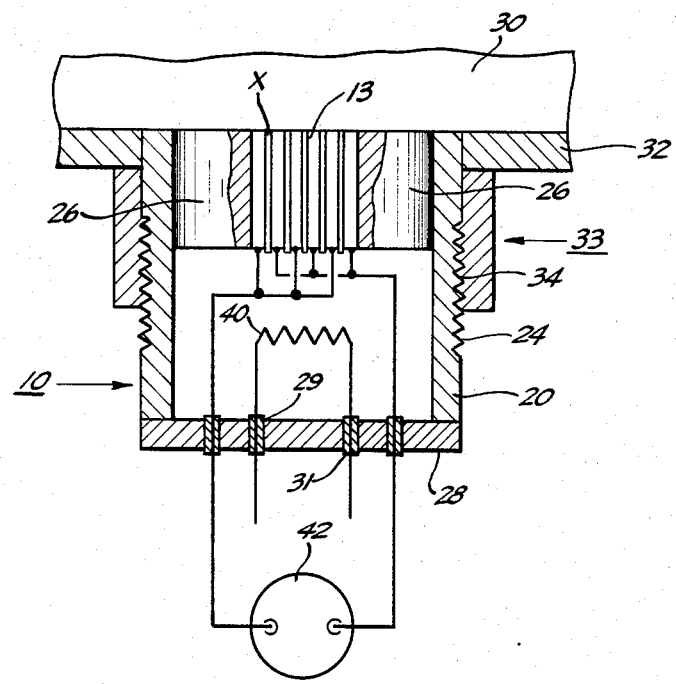
FIG. 1 is a cross-sectional, elevational view of the preferred embodiment of the liquid water sensor of this invention in its environment of use, i.e., inserted in a natural gas pipeline.

Referring now to FIGS. 1 and 2 a preferred embodiment of the liquid water sensor of this invention is shown generally at 10. The liquid water sensor includes a plurality of electrically conductive members 12a and 12b spaced from each other by an insulating medium 14 at a distance sufficient to enable a droplet or film of water to bridge at least two alternate conductive members and provide an electrically conductive pathway therebetween. For example, the conductive members are preferably spaced from about 0.001 to about 0.030 inches, and more preferably at about 0.003 inches. The conductive members are serially connected in alternate pairs to a power source (not shown). That is, the three conductive members 12a are serially connected and the three conductive members 12b are serially connected.

The novel liquid water sensor of this invention may be adapted for insertion into the wall of a natural gas pipeline by providing a hollow cylindrical housing 20 having an open end 22 and providing threads 24 or other securing means on the external surface of said hollow cylindrical housing.

A liquid water sensor of this invention is rigidly secured in said hollow cylindrical housing by an insulating means such as a ceramic material or a non-conductive polymer such as an epoxy 26. As shown, the edges 13 of said conductive members 12a and 12b are exposed to the interior 30 of the natural gas pipeline 32 with (as shown in FIG. 1) the liquid water sensor being provided in a lower portion of the natural gas pipeline, e.g., the six o'clock position or other location where liquid water is present in a gas being transported through said pipeline is likely to collect.

To secure the liquid water sensor in the pipeline, the pipeline is provided with a fitting 33 including a threaded connection 34 for receiving hollow cylindrical housing 20.

In a preferred embodiment of the instant invention, a heater 40, such as an electric heating coil, is provided for heating said conductive members to a temperature sufficient to evaporate water from the exposed edges 13. As has been noted above, it has been unexpectedly discovered that materials such as ferrous sulfide (which may be formed when hydrogen sulfide is present in the transported gas) may respond and falsely indicate the presence of liquid water by contacting the conductive members and providing an electrically conductive pathway therebetween. The heater 40 acts to evaporate water from the edges of the conductive members and indicate that the conductive pathway was indeed caused by liquid water rather than a non-volatile ferrous sulfide particle. If after heating for a sufficient time period to evaporate water, it appears that there is still a conductive pathway between the conductive members, the operator will be aware that the liquid water sensor of the instant invention is fouled and steps can be taken to clean or replace the liquid water sensor.

The closed end 28 of housing 20 is provided with a suitable number of apertures 29 to enable the liquid water sensor and the heater to be electrically connected to a suitable power source. The apertures may be provided with an insulating fitting 31 to prevent electrical contact between the housing 20 and the wiring for the sensor 10 and the heater 40.

In operation, the electrically conductive members 12a and 12b are placed in series with an electrical continuity detector (42) such as an ohmmeter or an ammeter. Both groups of electrically conductive members 12a and 12b may be the same material, e.g., aluminum or other similarly conductive material, in series with an ohmmeter to measure the decrease in resistance when droplet or film of water bridges at least one pair of adjacent members. Alternatively, electrically conductive members 12a and 12b may be metals having a different e.m.f., e.g. aluminum and copper, in series with an ammeter to measure the current flow when a droplet or film of water bridges at least one pair of adjacent members.

The insulating medium 14 may be polyethylene or other suitable non-conductive material. In one embodiment of this invention, the insulating medium 14 is eliminated, and the ceramic material or non-conductive polymer 26 extends between electrically conductive members 12a and 12b to function both as a means for securing the liquid water sensor in said housing 20 and as the insulating medium.

Figure 3:
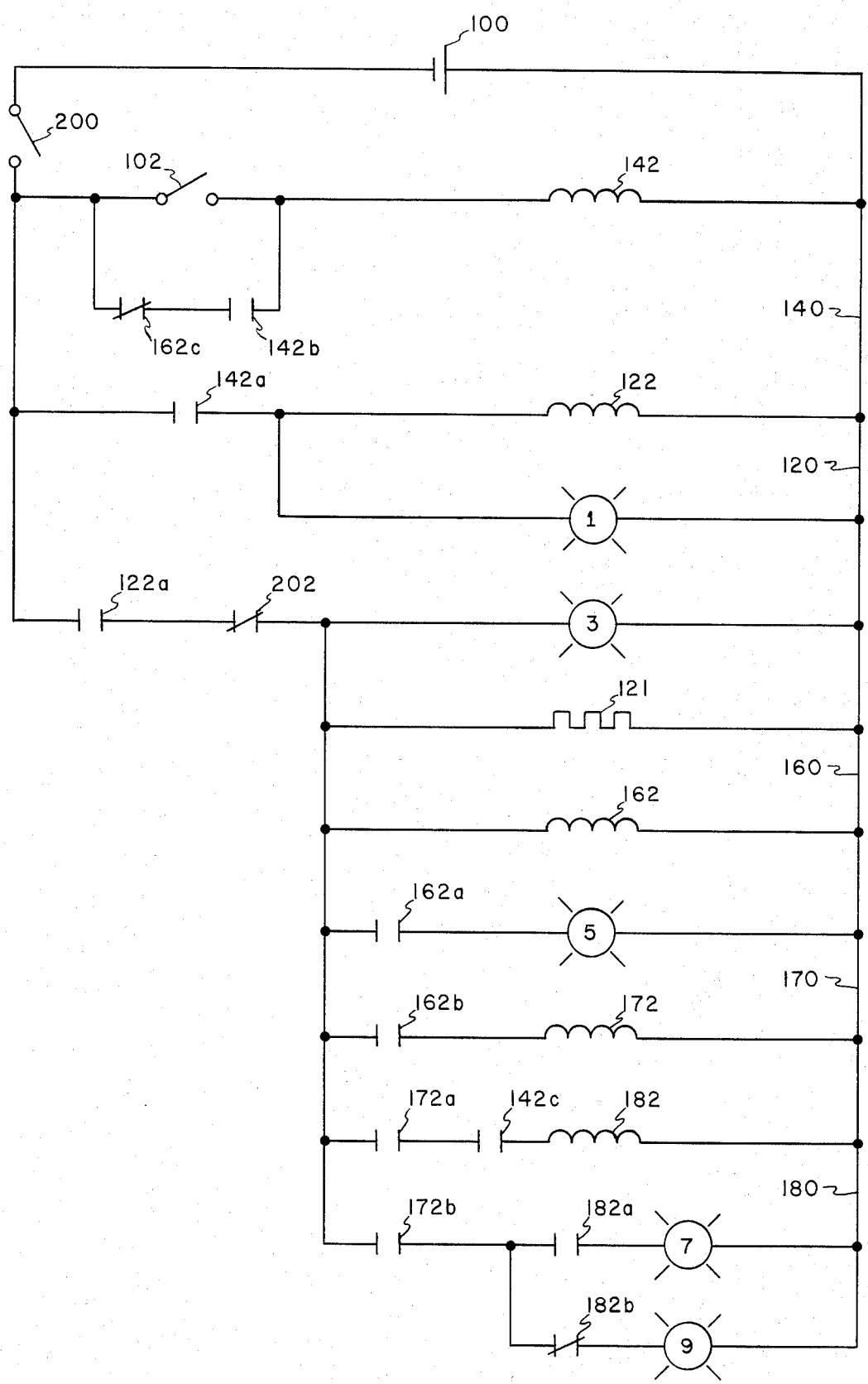
FIG. 3 is an electrical circuit diagram demonstrating the preferred method of electrically connecting the liquid water sensor to the heating element and the output circuit for indicating whether water or another conductive material having a boiling point higher than water is contacting the water sensor.

FIG. 3 shows a preferred embodiment for providing an electrical circuit including the liquid water sensor to determine whether the electrically conductive material providing a pathway between a conductive member is liquid water or if the liquid water sensor is fouled by ferrous sulfide or other conductive material having a boiling point greater than water.

In general, the circuit comprises a power supply 100, electric heater 121, and the above liquid water sensor or other detecting means 102 for sensing the conductivity of liquid water and other conductive materials, said liquid water sensor being disposed in operative relationship with said electric heater for heating said liquid water sensor and an electrical circuit, interconnected with said power supply, electric heater and the liquid water sensor, for controlling the heater in response to the liquid water sensor sensing a conductive material. The electrical circuit is operative to cause electric heater 121 to heat the liquid water sensor 102 for a sufficient period of time, after said liquid water sensor senses a conductive material, to vaporize water therefrom. The electrical circuit includes an output circuit for indicating the presence of water, or another conductive material having a boiling point higher than water.

In particular the liquid water sensor 102 acts as an electrical switch for sensing the conductivity of liquid water and/or conductive materials. The liquid water sensor 102 is included in a detecting circuit 140 which further includes, in series with said power supply, an alarm signal 1 and a sensor relay having a coil 142 and first, second and third independent, normally open electrical contacts 142a, 142b and 142c respectively. The first sensor relay contact 142a activates alarm signal 1 and a heater relay circuit 120. The sensor relay second contact 142b is a holding or interlocking contact to keep the sensor relay closed even if the liquid water sensor 102 momentarily signals that there is no contact with a conductive material. It should be pointed out that in a dynamic system, such as a pipeline, through which a gas is flowing, liquid water may be in contact with the liquid water sensor only momentarily before being swept away by the flowing gas. However, for the purpose of determining whether liquid water or a conductive material having a boiling point higher than water has contacted the liquid water sensor, it is important that sensor relay remain closed for at least a sufficient time period to ensure the evaporation of liquid water from the liquid water sensor. As shown, the sensor relay second contact 142b is in parallel with said water sensor 102 and said water sensor 102 and said sensor relay 102 second contact 142b are in series relationship to said power source 100 and said relay coil 142. The sensor relay third contact 142c in cooperation with the short time delay relay first contact (described below) activates an indicator circuit 180.

The heater relay circuit 120 will include an electrical heater 121, a 'heater on' signal 3 and a heater relay having a coil 122 and an independent, normally open electric contact 122a. The heater relay coil 122 and said sensor relay first contact 142a are in series with said power supply. The heater relay contact 122a activates 'heater on' signal 3 and electrical heater 121 as well as a long time delay circuit 160. As shown, the heater relay contact 122a and said electric heater 121 are in series with said power source 100 to enable power flow through said electrical heater after closure of said heater relay contact 122a 'Heater on' signal 3 is in parallel with said electrical heater 121 for activation of the 'heater on' signal when the electrical heater 121 is activated.

The long-time delay circuit 160 includes a long-time delay relay that is activated by the heater relay contact 122a and includes a coil 162 and first and third independent, normally open electrical contacts 162b and 162a, respectively, and a second independent, normally closed electrical contact 162c. The long-time delay coil 162 is in parallel relationship with electrical heater 121 to enable power flow through said long-time delay coil 162 simultaneously therewith.

Upon termination of a first preselected time period, sufficient to heat said sensor 102 to a temperature adequate to evaporate liquid water in contact therewith, the long time delay relay third contact 162a activates 'up to temperature' signal 5, the long time delay relay first contact 162b activates a short-time delay circuit 170, and the long time delay relay second contact 162c opens up the circuit containing sensor relay second contact 142b, i.e., the locking or holding contact, to enable the sensor relay to open if the liquid water sensor 102 is not in an electrically conductive condition. As shown, since said long-time delay relay second contact 162c is in series with said sensor relay first contact 142a the power flow through the heater relay coil 122 is interrupted, thereby deactivating the electrical heater 121.

The short time delay circuit 170 includes a short time delay relay having a coil 172 and first and second independent normally open contacts 172a and 172b, respectively. As shown, the short-time delay coil 172 is in series with said long-time delay relay first contact 162b to enable power flow therethrough. The short time delay relay first contact 172a, in conjunction with sensor relay third contact 142c activates the indicator relay of indicator circuit 180. The short-time delay relay second contact 172b activates either of the parallel signals 7 or 9 depending on whether the indicator relay is energized or not.

The indicator circuit 180 includes a relay having a coil 182 and a first independent normally open electrical contact 182a in series with indicator signal 7 and a second independent normally closed electrical contact 182b in series with indicator signal 9.

If the electrical switch of liquid water sensor 102 is closed, the sensor relay is energized and the normally open indicator relay contact 182a, i.e. the indicator relay first contact will close to activate signal 7 to indicate the sensor is fouled by contact with a conductive material having a boiling point higher than water. (Concomitantly, the normally closed second indicator relay contact will open to remove signal 9 from electrical continuity).

However, if the electrical switch of the sensor is open the normally closed contact 182b of the indicator relay will remain closed and signal 9 will be activated to indicate that electrical switch of the liquid water sensor is open, i.e., the water has been evaporated by an action of the heater on the conductive members and therefor water was present.

The above electrical circuit may include other modifications which are within the skill of one skilled in the art. For example, a reset switch 200 can be incorporated in such electrical circuit to permit the circuits of FIG. 3 to be turned off or activated as needed. A heater thermal limiting switch 202 may be incorporated in the electrical circuit of this invention for the purpose of insuring that the temperature of the heating element, in case of malfunction such as an internal short circuit, does not exceed a preset value.

While FIG. 3 shows a preferred embodiment of the circuit for automatically accomplishing the objective, which is to distinguish between the presence of liquid water and other electrically conducting material on the sensor, it is apparent that other means can also be used to accomplish the objective. For example, instead of the circuit of FIG. 3, the sensor switch 102 may be connected to an ohmmeter, and the heater 121 may be connected directly to its power source by means of a manually operated switch. If the ohmmeter indicates a conductive condition, an operator can manually activate the heater and then after a suitable time period (at which it is known that liquid water has been driven off the sensor) the operator can observe whether the ohmmeter still indicates a conductive condition. If it does, this indicates a fouling of the sensor with a non-volatile conductive material.

If liquid water sensor of the instant invention has indicated the presence of liquid water, steps may be taken to lower the dew point of the natural gas being transported to eliminate the liquid water from the pipeline and thus avoid corrosion by carbonic acid. For example, the dehydrating unit discussed above may be adjusted to remove a greater amount of water from the natural gas at the well head and thereby provide a natural gas capable of drying the pipeline.

The invention is further illustrated by the following example which is illustrative of a specific mode of practicing the invention and is not intended as limiting the scope of the appended claims.

EXAMPLE

A liquid water sensor consisting of 6 aluminum plates having the dimensions of 1/32 by one and one quarter by two inches and separated from each other by a polyethylene plastic membrane (each membrane being 0.003 inches thick) are in series with an ohmmeter. When dry, the electrical resistance across the assembled aluminum plates is infinite, i.e., greater than 10 megohms. However, when a droplet of distilled water is placed on the assembled plates at the edges thereof, so as to contact two or more of the edges the resistance falls to between 0.3 and 1.1 megohms. A droplet of tap water produces a resistance of 0.4 megohms and a droplet of 0.1 percent sodium chloride solution produces a resistance of 0.4 megohms across the aluminum plates. A higher concentration sodium chloride solution, i.e., one percent by weight sodium chloride, produces about 0.08 to 0.1 megohms resistance. It will be apparent to one skilled in the art that a reduction of the resistance from greater than ten megohms to 1.1 megohms or less may be utilized to trigger an alarm to indicate the presence of liquid water, or to directly indicate the presence of liquid water. Furthermore, one may substitute another suitable continuity measuring device such as an ammeter to detect conductivity between the plates, provided the plates themselves form an electrical battery with a water droplet i.e., the plates may be of alternating metals of dissimilar e.m.f. such as copper and aluminum.

Moreover, it is clear that a heating element can be provided in conjunction with said conductive plates to heat the edges thereof and evaporate water therefrom. Thus, conductive materials having a boiling point greater than water will remain as a conductive pathway between alternate plates, and consequently, measuring the conductivity before and after heating will indicate whether liquid water or a conductive material having a boiling point greater than water is in contact with the plates.

While particular embodiments of the invention have been described it will be understood of course that the invention is not limited thereto since many obvious modifications can be made and it is intended to include within this invention any such modification as will fall within the scope of the appended claims.

Having now described the invention, I claim:

1. A liquid water sensor for use in a pipeline utilized to transport a carbon dioxide-containing gas which comprises:
    (a) a plurality of conductive members spaced from each other by an insulating medium, said conductive members being serially connected in alternating pairs, and
    (b) a continuity detector being serially connected to each pair of conductive members, wherein said conductive members are spaced at a distance enabling a droplet or film of water to bridge at least two alternate conductive members to provide a conductive pathway therebetween.

2. The sensor of claim 1 wherein said conductive members comprise aluminum plates.

3. The sensor of claim 2 wherein said insulating medium comprises polyethylene film.

4. The sensor of claim 3 wherein said continuity detector is an ohmmeter.

5. The sensor of claim 3 wherein said distance is about 0.003 inches.

6. The sensor of claim 1 additionally comprising means for heating said conductive members to evaporate liquid water therefrom.

7. The sensor of claim 1 wherein one pair of said conductive members comprises aluminum and the other pair of conductive members comprises copper.

8. The sensor of claim 7 wherein said continuity detector is an ammeter.

9. The sensor of claim 1 wherein said distance is from about 0.001 to about 0.030 inches.

10. A liquid water sensor for use in a pipeline utilized to transport a carbon dioxide-containing gas which comprises:
    (a) a plurality of conductive members spaced from each other at a distance from about 0.001 to about 0.030 inches by an insulating medium, said conductive members being serially connected in alternating pairs, and
    (b) a continuity detector serially connected to each pair of conductive members.

11. The liquid water sensor of claim 10 wherein said conductive members comprise alternating aluminum and copper plates and said insulating medium is a ceramic material.

12. A liquid water sensor for inserting into a natural gas pipeline and detecting liquid water in the presence of other conductive materials having a boiling point higher than water which comprises:
    (a) a hollow cylindrical housing having an open end and being adapted for insertion into the wall of a natural gas pipeline with said open end exposed to the interior of said natural gas pipeline, (b) a plurality of conductive members spaced from each other and serially connected in alternating pairs, each of said conductive members being located within said housing and having an edge adapted to be exposed to the interior of a natural gas pipeline, and each edge being spaced from adjacent edges at a distance enabling bridging by a drop or film of water to provide a conductive pathway therebetween, (c) a heating element in proximity to said conductive members and adapted to heat said conductive members to a temperature sufficient to evaporate water from the exposed edges, (d) an insulating medium spacing each conductive member from adjacent conductive members and rigidly affixing said conductive members and said heating element within said housing, (e) means for electrically connecting said conductive members to a continuity detector, and (f) means for connecting said heating element to a power source.

13. The liquid water sensor of claim 12 wherein said conductive members comprise aluminum plates and said insulating medium is a ceramic material.

14. The liquid water sensor of claim 13 wherein said distance is about 0.003 inches.

15. The liquid water sensor of claim 12 wherein said distance is from about 0.001 to about 0.030 inches.

16. An electrical circuit for detecting liquid water in the presence of other electrically conductive materials having a boiling point higher than water comprising:

(a) a power supply, (b) an electric heater, (c) detecting means for sensing the conductivity of liquid water and other conductive materials, said detecting means being disposed in an operative relationship with said electric heater for heating said detecting means, and (d) circuit means, interconnected with said power supply, electric heater and detecting means for controlling the heater in response to the detecting means sensing a conductive material, said circuit means being operative to cause the heater to heat the detector, for a preselected period of time after the detecting means senses a conductive material to vaporize water therefrom, said circuit means including output circuit means for indicating the presence or non-presence of water.

17. An electrical circuit for detecting liquid water in the presence of other electrically conductive materials that may foul a liquid water sensor such as conductive materials having a boiling point higher than water comprising:

(a) a power supply, (b) an electric heater, (c) detecting means, including an electrical switch, for sensing the conductivity of liquid water and other conductive materials, said detecting means being disposed in an operative relationship with said electric heater for heating said detecting means, and (d) circuit means comprising:

(i) a sensor relay having a coil and first, second and third independent normally open electrical contacts, (ii) a heater relay having a coil and a normally open contact, (iii) a long-time delay relay having a coil and an independent normally open electrical contact and a second independent normally closed electrical contact, (iv) a short-time relay having a coil and first and second independent normally open electrical contacts, (v) an indicator relay having a coil and a first independent normally open electrical contact and a second independent normally closed electrical contact, (vi) a fouled signal, and (vii) a water signal, said detecting means switch and said sensor relay coil being connected in series with said power supply, said long-time delay second contact and said sensor relay second contact being connected in parallel with said detecting means switch to enable continuous power flow through the sensor relay coil after closure of the detecting means switch despite momentary opening the detecting means switch, said sensor relay first contact and said heater relay coil being connected in series with said power supply to enable power flow through the heater relay upon closure of said detecting means switch, said heater relay contact and said electric heater being in series with said power source to enable power flow through said electric heater after closure of said heater relay contact, said long-time delay relay coil being connected in parallel with said electric heater, to enable power flow through said long-time delay relay coil, said long-time delay second contact being in series with said sensor relay first contact to discontinue power flow through said heater relay coil upon termination of a first preselected time period, said long-time delay relay first contact being in series with said short-time delay relay coil to enable power flow through said short-time delay relay coil upon termination of said preselected time period, said short-time delay relay first contact, said sensor relay third contact and said indicator relay coil being in series to enable power flow through said indicator relay coil upon termination of a second preselected time period, said short-time delay relay second contact, said indicator relay first contact and said fouled signal being connected in series and said indicator relay second contact and said water signal being connected in parallel to said indicator relay first contact to enable either power flow through said 'fouled' signal or said 'water' signal upon termination of said second preselected time period.

18. A method for preventing corrosion in a pipeline utilized to transport a carbon dioxide-containing gas which comprises:

(a) providing a liquid water sensor at a place in said pipeline where liquid water is likely to collect, said liquid water sensor comprising (i) a plurality of conductive members spaced from each other by an insulating medium, said conductive members being serially connected and spaced at a distance enabling a droplet or film of water to bridge said conductive members to provide a conductive pathway therebetween and (ii) a continuity detector serially connected to each conductive member;

(b) monitoring said water sensor for the presence of liquid water, and (c) adjusting the dew point of said gas to remove said liquid water.

19. A liquid water sensor for inserting into a natural gas pipeline and detecting liquid water in the presence of other conductive materials having a boiling point higher than water which comprises:
(a) a plurality of conductive members spaced from each other by an insulating medium, said conductive members being serially connected and spaced from each other at a distance enabling a droplet or film of water to bridge said conductive members to provide a conductive pathway therebetween, and
(b) a heating element in proximity to said conductive members and adapted to heat said conductive members to a temperature sufficient to evaporate water therefrom.

* * * * *